(12) United States Patent
Ng et al.

(10) Patent No.: US 10,952,609 B2
(45) Date of Patent: Mar. 23, 2021

(54) APPARATUS FOR MODELLING OCULAR STRUCTURES

(71) Applicant: Novartis AG, Basel (CH)

(72) Inventors: Eugene Ng, Dublin (IE); Alexander Goncharov, Galway (IE); Patrick Collins, Dublin (IE)

(73) Assignee: Alcon Inc.

( * ) Notice: Subject to any disclaimer, the term of this patent is extended or adjusted under 35 U.S.C. 154(b) by 224 days.

(21) Appl. No.: 16/054,653

(22) Filed: Aug. 3, 2018

(65) Prior Publication Data
US 2018/0344157 A1    Dec. 6, 2018

Related U.S. Application Data

(63) Continuation of application No. 14/676,777, filed on Apr. 1, 2015, now abandoned, which is a continuation
(Continued)

(51) Int. Cl.
*A61B 3/14* (2006.01)
*A61B 3/107* (2006.01)
(Continued)

(52) U.S. Cl.
CPC ............ *A61B 3/14* (2013.01); *A61B 3/1005* (2013.01); *A61B 3/107* (2013.01); *A61B 3/145* (2013.01);
(Continued)

(58) Field of Classification Search
CPC .......... A61B 3/14; A61B 3/145; A61B 3/107; A61B 3/135; A61B 3/158; A61B 3/18;
(Continued)

(56) References Cited

U.S. PATENT DOCUMENTS

| | | | | |
|---|---|---|---|---|
| 4,443,075 A | * | 4/1984 | Crane | A61F 9/00821 351/207 |
| 2007/0129775 A1 | * | 6/2007 | Mordaunt | A61F 9/008 607/88 |

(Continued)

FOREIGN PATENT DOCUMENTS

WO    2010109020 A1    9/2010

OTHER PUBLICATIONS

Patricia Rosales and Susana Marcos, "Phakonnetry and lens tilt and decentration using a custom-developed Purkinje imaging apparatus: validation and measurements," J. Opt. Soc. Am. A 23, 509-520 (2006 (Year: 2006).*

(Continued)

*Primary Examiner* — Marin Pichler
*Assistant Examiner* — Alberto J Betancourt

(57) ABSTRACT

An imaging system for an optical element, the imaging system comprising means for illuminating a targeted optical element with at least one incident light beam and means for directing at least two light beams returning from at least one surface of the illuminated optical element onto a detector; the detector adapted to measure relative light characteristics of the at least two returning light beams and to calculate at least one parameter of the optical element using the measured characteristics of the at least two returning light beams.

12 Claims, 18 Drawing Sheets

Related U.S. Application Data of application No. 14/007,353, filed as application No. PCT/EP2012/055358 on Mar. 26, 2012, now abandoned.

(60) Provisional application No. 61/467,836, filed on Mar. 25, 2011.

(51) Int. Cl.
*A61B 3/10* (2006.01)
*A61B 3/135* (2006.01)
*A61F 9/008* (2006.01)

(52) U.S. Cl.
CPC ..... *A61B 3/135* (2013.01); *A61F 2009/00878* (2013.01)

(58) Field of Classification Search
CPC .... A61B 3/13–135; A61B 3/1005–112; A61B 3/117–125; A61B 3/102; A61B 3/1025; A61B 3/12–125; A61B 3/103–1035; A61B 3/11–112; A61F 2009/00878
USPC ................ 351/205–208, 213–215, 219–221, 351/245–247
See application file for complete search history.

(56) References Cited

U.S. PATENT DOCUMENTS

| 2011/0105943 A1* | 5/2011 | De Paz Sicam ..... A61B 3/1005 600/558 |
| 2012/0026466 A1* | 2/2012 | Zhou ...................... A61B 3/102 351/214 |

OTHER PUBLICATIONS

Rosales, P., De Castro, A., Jimenez-Alfaro, I. and Marcos, S. (2010), Intraocular lens alignment from Purkinje and Scheimpflug imaging. Clinical and Experimental Optometry, 93: 400-408 (Year: 2010).*

* cited by examiner

APPARATUS FOR MODELLING OCULAR STRUCTURES

CROSS-REFERENCE TO RELATED APPLICATIONS

This application claims priority to U.S. patent application Ser. No. 14/676,777 filed on Apr. 1, 2015, which is incorporated herein by reference, which claims priority to U.S. patent application Ser. No. 14/007,353 filed on Sep. 25, 2013, which is incorporated herein by reference, and which is a national stage application of PCT Application Number PCT/EP2012/055358 that has an International filing date of Mar. 26, 2012, which is incorporated herein by reference, and which claimed priority from U.S. Provisional Application No. 61/467,838 filed on Mar. 25, 2011, which is incorporated herein by reference.

TECHNICAL FIELD

The present disclosure includes descriptions of technology that relates to ocular modelling.

BACKGROUND

Ocular procedures often modify one or more structures of the eye, such as the cornea, lens, or retina. Some procedures involve removing or replacing one or more structures of the eye, or adding an implant. For example, lens replacement surgery involves removing a patient's existing lens and replacing it with a new lens. Some procedures, such as laser vision correction surgery, do not remove or replace existing structures of patient's eye, or add an implant to the eye, but rather re-shape existing structures. Regardless of the type of modification being made (e.g., removal, replacement, insertion, or alteration), the optical performance of the eye is altered by adjustments made to the structures of the eye. Therefore in order to accurately model the structure of any eye, it is necessary to determine the ocular parameters of that eye. These parameters include shape, thickness, and refractive index of ocular structures such as the cornea, the lens, the retina, or any other structures of interest.

Measuring parameters such as curvatures, or shapes of surfaces, or thicknesses of elements within a patient's eye is traditionally carried out using variations of ultrasound Optical Coherence Tomography (OCT) Interferometery, Purkinje, or Scheimpflug systems.

Typical Scheimpflug systems facilitate diagnosis of the front chamber of the eye. U.S. Pat. No. 6,286,958 B1 entitled "Device for the examination of an eye using a Scheimpflug camera and a slit light projector for photographing slit images of an eye" for example discloses a classic single Scheimpflug system configured for examination of the eye only one meridian at a time.

US 2009/0190093 entitled "Dual Scheimpflug System for Three-Dimensional Analysis of an Eye" comprises a pair of rotating Scheimpflug cameras positioned perpendicular to one another and rotatable on a platform to generate and display a three dimensional representation of the anterior corneal surface, posterior corneal surface, anterior iris surface and anterior lens surface. While this system provides a dual system, it implements the system using two separate cameras and it is not possible to provide the possibility of allowing two cross sections of the cornea and crystalline lens to be obtained simultaneously.

A disadvantage of these systems is the inability to measure all the relevant parameters of the eye in a single pass and without having to move or re-orientate the equipment. These systems are unable to measure the front of the lens of the eye without dilating the pupil and also the back surface of the lens under most conditions even with dilation of the pupils. It will be appreciated that dilation affects the accuracy of any measurements made.

It is therefore an object of the present invention to provide an imaging system which enables measurement of all relevant parameters of the eye necessary for ocular modelling in a single pass without having to move or re-orientate any part of the imaging system, i.e. to measure the optical parameters of the eye necessary to compile an individual optical model. It is a further object of the present invention to increase the efficiency and accuracy of ocular models by improving the accuracy of the measurements made.

It would be desirable to measure the following:
Posterior and anterior curvature of the Cornea
Posterior and anterior curvature of the lens
The Refractive index of the Cornea, Aqueous humor, lens, vitreous humor
Gradient index of cornea and lens
The thickness of the cornea and lens
The Anterior chamber depth (thickness of the aqueous humor)

Current OCT and Scheimpflug cameras measure the curvatures and thicknesses of surfaces within a patients eye. However, these measurements do not correct for the optical effects of the preceding optical surfaces accurately.

Refractive index is a core parameter needed for ocular modelling. All prior art ignores inter-subject variation in refractive index. Failure to resolve refractive index leads to errors in all measurements beyond the first optical surface (cornea).

SUMMARY

The present invention provides an imaging system for an optical element, the imaging system comprising: means for illuminating a targeted optical element with at least one incident light beam; and means for directing at least two light beams returning from at least one surface of the illuminated optical element onto a detector; the detector adapted to measure relative light characteristics of the at least two returning light beams and to calculate at least one parameter of the optical element using the measured characteristics of the at least two returning light beams.

The optical element may be a multiple element or system. Light returning from the optical element may be returning though reflection, scatter, refraction, fluorescence or a combination of these.

The means for illuminating the targeted optical element preferably comprises at least one source and optical means for altering the direction of incidence of at least one incident light beam on the targeted optical element.

The system may further comprise means for splitting at least one beam of light emitted from the source, wherein at least two of the resultant split beams have a different angle of incidence relative to the optical axis of the targeted optical element.

The optical means may comprise at least one or more of a beam shaping lens, mirror with optical power, fold mirror, beam splitter and/or prism.

The system may further comprise means for changing at least one characteristic of at least one incident light beam on the targeted optical element between consecutive measurements of the detector. These may include, for example, means for changing the direction of incidence of at least one incident light beam on the targeted optical element between consecutive measurements of the detector. Thus through use of this system, changes of the system can occur from measurement to measurement within an entire examination of a single eye. The examination of a single eye can contain one or more measurements while a measurement is where the state of the device is frozen, i.e. beam angle at one particular angle, and then the next measurement of the examination will have an altered angle. It is also possible that an examination of a single eye can consist of a single measurement where nothing has change as yet can still yield results of the parameters of the eye. Also, other examinations can have more than one measurement where the system changes a parameter like the angle of the beam and the results will yield the parameters of the eye.

The relative light characteristics of the source might include, but is not limited to, at least one of the following characteristics: spatial and temporal intensity distributions, positions, spatial and temporal linear and/or circular polarizations, phases, wavelengths, temporal and spatial coherences, speckles structures, scattering coefficients and/or the g-anisotropy factors.

Likewise, the measured characteristics of the illuminating and/or returning light comprise at least one of spatial and temporal intensity distribution, position, spatial and temporal linear and circular polarization, degree of polarization, phase, wavelength, temporal and spatial coherence, speckles structure, scattering coefficient and g-anisotropy factors.

The optical device may comprise means for varying the direction of illumination of the optical element relative to the axis of the optical element, being adapted to control the direction of at least one incident light beam.

Mirrors, lenses, prisms, diffracting gratings and/or coherent fibre bundles may be used to vary or control the direction of illumination of the optical element relative to the axis of the optical element.

Means may be provided to select different beams illuminating the optical element. By which this might include, but is not limited to apodization of a large illuminating beam using masks in filter wheel and/or a spatial light modulator, selection of various smaller illuminating beams with temporal and/or spatial control.

The means for directing at least two light beams returning from at least one surface of the illuminated optical element onto the detector may comprise at least one optical component.

The optical component may comprise one or more of the following: mirrors, lenses, prisms, diffracting gratings, coherent fibre bundles which will receive the returning light at particular angles and positions relative to the axis of the optical element.

The relative light characteristics of the returning light beams might include, but is not limited to, at least one of the following characteristics: spatial and temporal intensity distributions, positions, spatial and temporal linear and circular polarizations, degree of polarizations, phases, wavelengths, temporal and spatial coherences, speckles structures, scattering coefficients and/or the g-anisotropy factors.

The or each optical component may be further adapted to control the direction of at least one incident light beam. The or each optical component may be used in part to direct the returning light to the detector(s).

Preferably the detector is a CCD, a CMOS sensor, a human eye, a photographic plate, a channel plate array, avalanche photodiodes, a scintillation detector or a photomultiplying tube.

The system may further comprise means for changing the position of the detector to focus any or all of the returning light.

The characteristics of the illuminating and/or returning light are not limited to a single parameter within its own characteristic. The characteristics may include at least one of spatial and temporal intensity distributions, positions, spatial and temporal linear and circular polarizations, degree of polarizations, phases, wavelengths, temporal and spatial coherences, speckles structures, scattering coefficients and/or the g-anisotropy factors and may be used sequentially or simultaneously. Other characteristics may be used however.

The characteristics of the illuminating and/or returning light preferably comprise at least one of spatial and temporal intensity distribution, position, spatial and temporal linear and circular polarization, degree of polarization, phase, wavelength, temporal and spatial coherence, speckles structure, scattering coefficient and g-anisotropy factors.

The system may further comprise a second detector. The first detector and the second detector may lie on different planes with respect to the optical axis of the targeted optical element. The first detector and the second detector may however lie on the plane of the optical axis of the targeted optical element.

Two or more detectors can lie in any plane location and orientation such as to fulfill the Scheimpflug condition. Two detectors may be placed orthogonally. Preferably, in this embodiment, the means for illuminating comprises a cross hair light source adapted to generate two beams for projection on the optical element.

The present invention further provides a method of imaging an optical element, the method comprising the steps of: illuminating a targeted optical element with at least one incident light beam; and directing at least two light beams returning from at least one surface of the illuminated optical element onto a detector; measuring the relative light characteristics of the at least two returning light beams and calculating at least one parameter of the optical element using the measured characteristics of the at least two returning light beams.

The method may further comprise controlling the direction of the incident light beam. The method may further comprise changing or varying the direction of illumination of the optical element relative to the axis of the optical element.

The method may further comprise changing the position of a detector to focus any or all of the returning light. The characteristics of the illuminating and/or returning light comprise at least one of spatial and temporal intensity distribution, position, spatial and temporal linear and circular polarization, degree of polarization, phase, wavelength, temporal and spatial coherence, speckles structure, scattering coefficient and g-anisotropy factors.

The method may also comprise changing the direction of incidence of at least one incident light beam on the targeted optical element between consecutive measurements.

The present invention as provided herein provides control of probing beams that fulfill ray tracing criteria and that are capable of being isolated by the telecentric imaging to an accurate model of the eye. In order to meet this objective, all meridians are obtained simultaneously or as close to simultaneous as possible. In one embodiment simultaneously is considered as less than 1.0 second and preferably under 0.5 seconds.

The present invention also allows the location of visual axis on images to be determined by having a fixation target eye tracking, or otherwise, which is critical for ray tracing.

By providing angle of incident beams of less than forty degrees, images of the entire lens may be obtained, even in smaller pupils. This truncation of the beam height also allows for additional data points to enable ray tracing.

Iterative and reiterative ray tracing calculations are also described which are common to all optical instruments in order to accurately derive ocular surface curvatures, thickness and refractive index. Specifically these calculations take into account the optical design of the instruments and the optics of the elements of the eye preceding the surface under consideration.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

Various non-limiting embodiments of the technology described herein will now be described with specific reference to the following figures. It should be appreciated that the figures are not necessarily drawn to scale.

DETAILED DESCRIPTION

Apparatus and methods for modelling one or more structures of the eye are described. The modelling may indicate the shape and/or location of the structures of the eye, which may be determined using optical methods for determining one or more parameters of the ocular structure of interest, as well as of the structures preceding the ocular structure of interest. The one or more parameters may include shape, thickness, distances and refractive index.

The measurement of any one of shape, thickness and/or refractive index of an ocular structure of interest may depend to some extent on the directional changes which light employed by the measurement technique undergoes while passing through any ocular structures preceding the structure of interest. Thus, according to one aspect of the technology, measurements of shape, thickness, and/or refractive index of ocular structures may be corrected to account for the dependence of the measured values on the other parameters for that structure, as well as on any of the parameters of preceding structures.

The aspects of the technology mentioned above, as well as additional aspects, will now be described in greater detail. These aspects may be used individually, all together, or in any combination of two or more, as the technology is not limited in this respect.

As mentioned, according to one aspect of the technology described herein, the shapes and locations of ocular structures may be determined, from which an accurate model of the eye may be made. The structures may include the cornea, the lens, the retina, or any other structures of interest. The shape and location of a structure may be determined by direct measurement of one or more parameters, including shape, thickness, and refractive index, and then correction of any measurements to account for dependence on other parameters of the measured structure or on any parameters of other structures within the eye may be performed. An example is now described in connection with FIG. 1.

Figure 1:
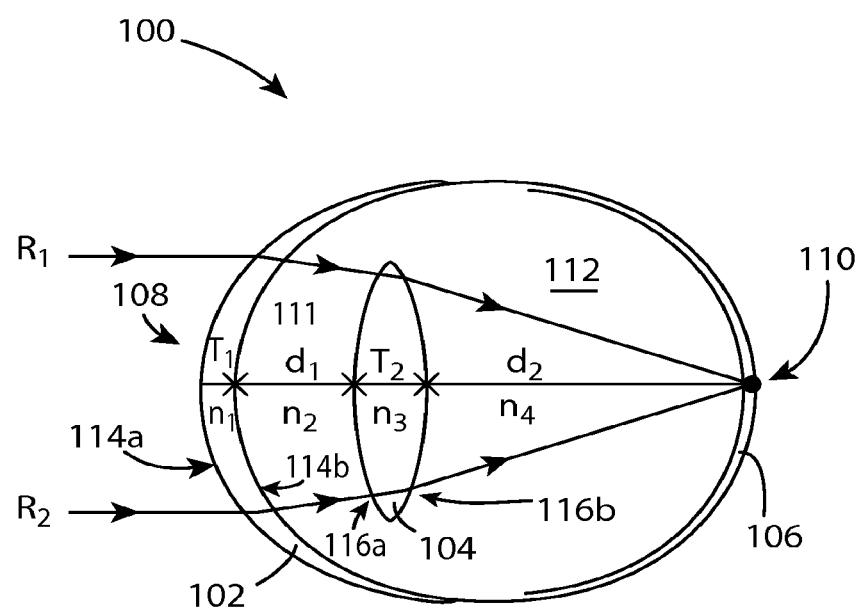
FIG. 1 is a simplified schematic of an eye.

FIG. 1 provides a simplified representation of an eye 100, including a cornea 102, a lens 104, and a retina 106. These structures are arranged between a front side 108 of the eye, where light enters, and a back side 110 of the eye. Between the cornea 102 and the lens 104 is a volume of aqueous 111. Between the lens 104 and the retina 106 is a volume of vitreous 112. It should be appreciated that the eye 100 is simplified for purposes of illustration, and that eyes typically include more features than those shown in FIG. 1.

A structure of interest may be a complete structure (e.g., a lens) or a surface (e.g., the front of the lens) and a parameter may be the shape, thickness, or refractive index of the structure of interest. Any of these three parameters may be of interest either as an ultimate result or as a means for determining other parameters, or for both purposes. For example, the shape of the cornea may be of interest as an end result for modelling the cornea, but may also facilitate determination of the refractive index of the cornea.

As mentioned, modelling the eye 100 may involve determining the shape of one or more surfaces of interest, such as the front surface 114a of the cornea, the back surface 114b of the cornea, etc. Topography, for example Scheimpflug topography, is one technique that may be used to determine the shapes of such surfaces. However, as mentioned above other methods, including Purkinje imaging, interferometry and/or optical coherence tomography may also be used.

As also mentioned, modelling the eye 100 to provide locations of the ocular structures may involve determining various distances within the eye. As shown, the cornea 102 has a thickness Tl, between the front surface 114a of the cornea and the back surface 114b of the cornea, and lens 104 has a thickness T2, between the front surface 116a of the lens and the back surface 116b of the lens. The cornea and lens are separated by a distance dl (i.e., the distance from the back surface 114b of the cornea and the front surface 116a of the lens). The retina is separated from the back surface 116b of the lens by a distance d2. Such distances may be measured using OCT, or other techniques, as the various aspects described herein are not limited in this respect.

However, while standard topography and interferometry techniques may be used to measure shapes and distances of ocular structures, such direct measurement techniques alone may not produce entirely accurate results. The light employed by such measurement techniques may undergo directional changes induced by the varying indices of refraction of the ocular structures (i.e., refractive index nl of the cornea, refractive index n2 of the aqueous, refractive index n3 of the lens, and refractive index n4 of the vitreous gel), such that the results may not be accurate if not accounting for such directional changes.

Figure 2:
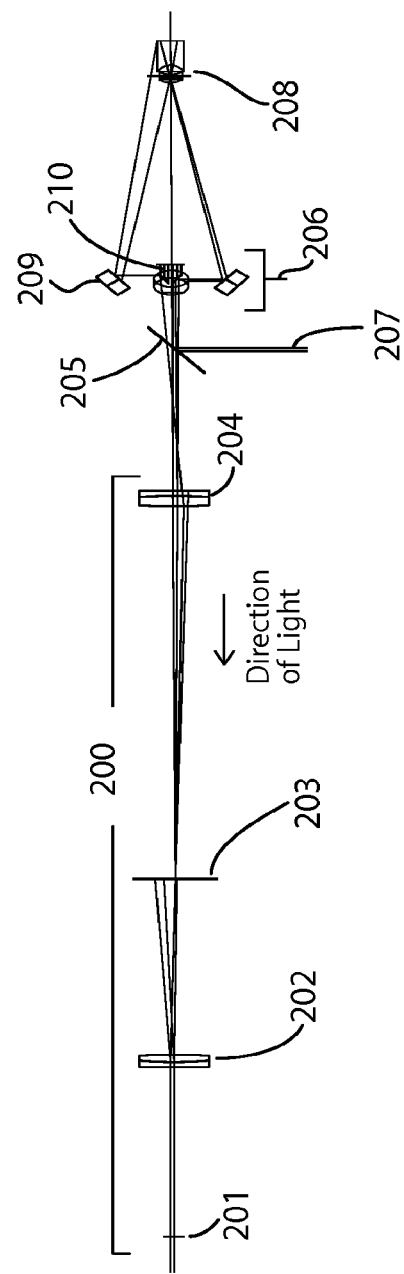
FIG. 2 depicts a layout of imaging and probing sections of a Purkinje system in accordance with one embodiment of the present invention.

In one embodiment of the present invention a modified Purkinje imager such as that shown in FIG. 2 is used to obtain measurements of the ocular parameters. As shown in FIG. 2 an illuminating beam from a collimated source is injected into the system to illuminate mirrors, 210 which are located on the optical axis. These mirrors, 210 as shown in FIG. 2 are rod mirrors. However, it will be appreciated that they are not restricted as such and may also include any reflective element including a combination of prisms (utilizing total internal reflection) with or without mirrors, or glass cones (axicons). It will be appreciated, however, that refractive prisms and glass axicons may introduce unwanted intrinsic aberrations, whereas flat mirrors are free from aberrations. Illumination of the rod mirrors 210 can be achieved using a beam splitter 205.

When rays from the source fall on the mirrors 210, these rays are then reflected such that the rays are directed to a system of meridional flat mirrors 209. The combination of mirrors, 209, 201 are herein referred to as "Mirricon", 206. The Mirricon, 206 is configured both for illumination of the eye with collimated beams off-axis and also for imaging the Purkinje reflections working in conjunction with a telecentric optical system or arm 200. The Mirricon can deliver the Purkinje reflections to the telecentric system in such a way as to reduce the angular separation of Purkinje reflections from opposite beams such that intrinsic aberrations of the telecentric system are reduced.

The mirrors 209 are angularly orientated with respect to the mirrors 210 on opposing sides of the optical axis. The rays are then directionally reflected from the mirrors 209 towards an eye, 208 at a specific angle of reflection selected such that the Purkinje reflections should be present in the image and separated from each other by sufficient magnitude such that the reflections are resolvable in the crowded group. It will be appreciated that the optimal values for the off-axis angles of the beams depend also on the subject's eye biometry. Further details of the beam angle is provided in relation to FIG. 3.

After the illuminating beam has been injected into the Mirricon 206 and thus onto the eye, 208, the returning light passes to the telecentric imaging arm 200. The telecentric imaging arm 200 comprises four main components, including a collimating lens 204, an imaging lens, 202, a telecentric aperture stop, 203 and a detector 201, which may be a charge coupled device (CCD) or other camera. The telecentric imaging arm delivers the Purkinje reflections onto the detector. The combination of lenses, 202 and 204 and telecentric stop aperture act to block any rays that are not parallel to the optical axis of the system striking the detector 201.

Figure 3:
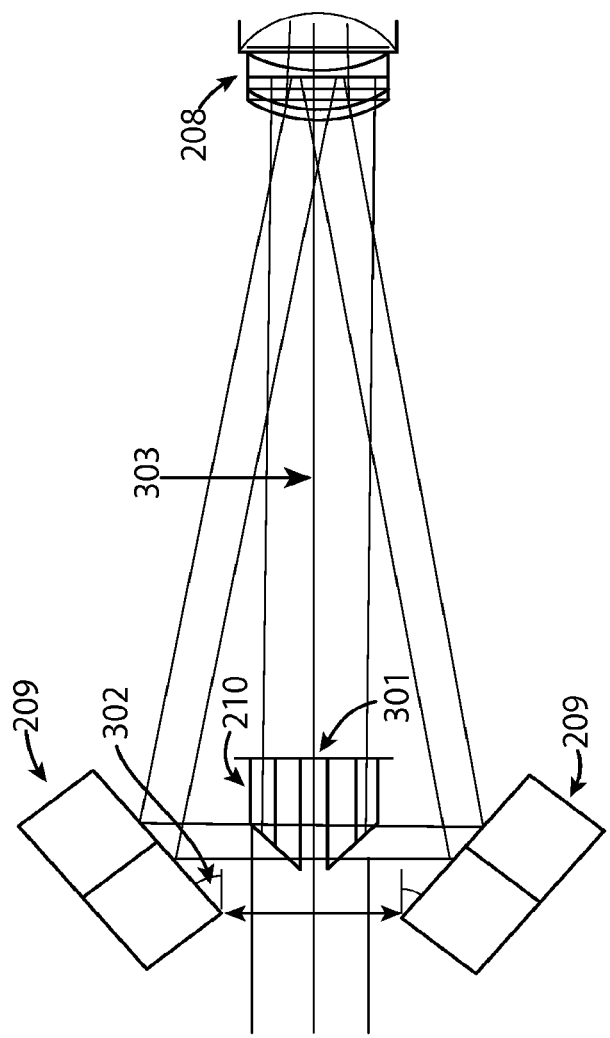
FIG. 3 is a more detailed view of the device for controlling the illuminating and returning beams seen in FIG. 2 in accordance with the present invention.

The mechanics of the Mirricon 206 are described in further detail in FIG. 3. The Mirricon is the beam control unit for the Purkinjie imager in accordance with the present invention. Either coherent LASER or incoherent LED light may enter form the left or right of the rod mirrors, 210. As shown in FIG. 3, these rod mirrors are 45-degree rod mirrors. A gap 301 exists between the rod mirrors allowing a portion of the light to pass directly between the mirrors. Reflected light is also bounced from the rod mirrors 210 to the meridional beam control mirrors, 209. These beam control mirrors then alter the reflected light to generate an input beam angle 302. This input beam angle can range from 0 to 90 degrees and can be generated by any combination of the rod mirror and beam control angles provided that the final input beam angle is within the defined range. The rod mirrors 210 and the meridional beam control mirrors are disposed on opposing sides of the instrument's optical axis.

Illumination of the surfaces in question can be done with any wavelength beam of any type, be that coherent laser light, partially coherent LED light or an incoherent broadband source. It is preferable to use the narrowest of bandwidths so that the dispersion of the medium will not be a spectral blur of the spot on the detector.

The manipulation of this collimated beam can be done by many possible mean, directed beams, a refracted beam by an axicon or a reflected beam by an arrangement of minors. The minor solution is of particular interest as it does not induce dispersion or optical aberrations as the axicon would. It also allows for a smaller diameter illumination beam saving on the source intensity and allowing for the telecentric imaging arm to use physically smaller optics.

Figure 15:
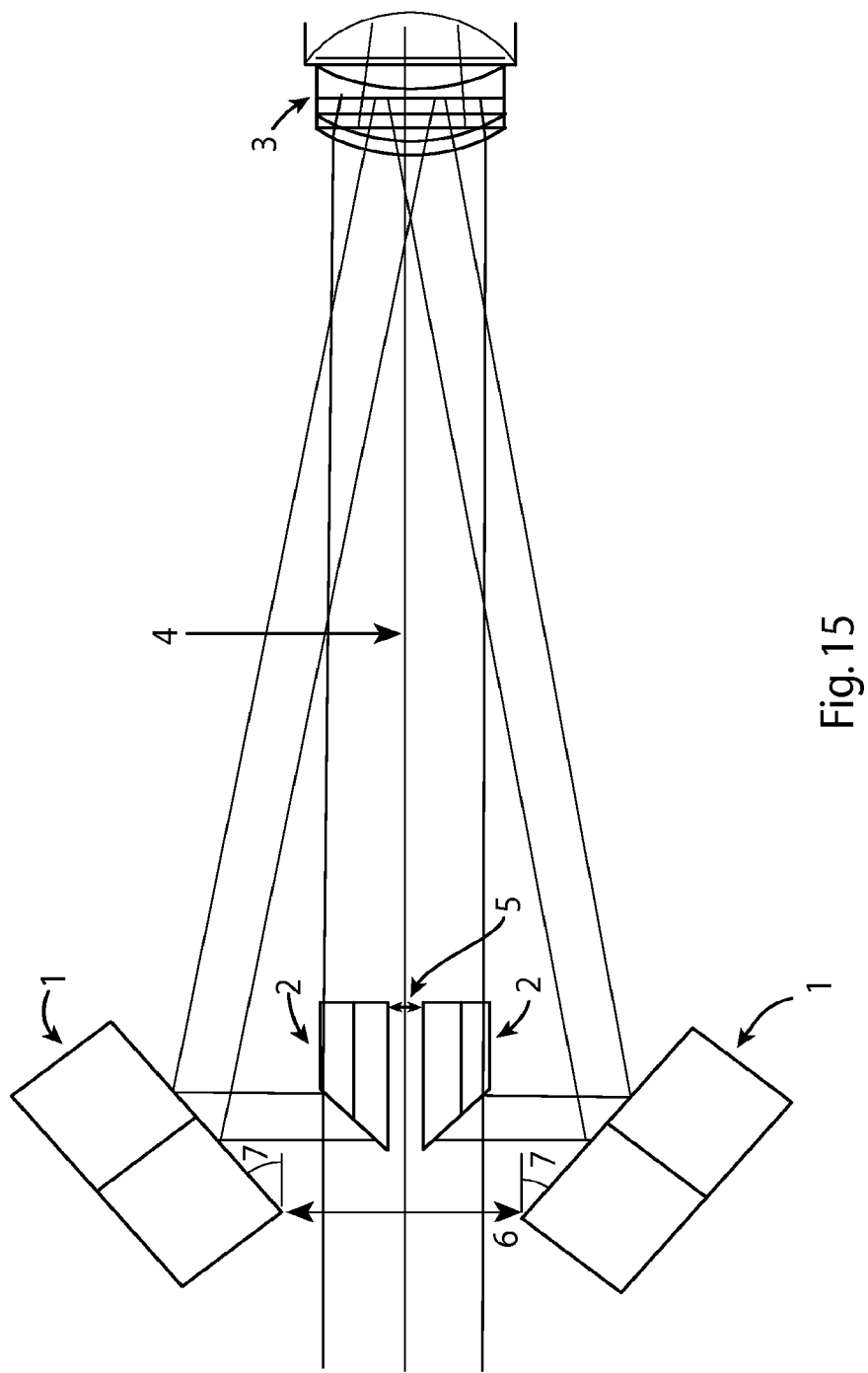
FIG. 15 shows a ray-tracing view of FIG. 3 depicting the illuminating beams in accordance with the present invention.

FIG. 15 is a representation of the mirrored beam control, here named as the mirricon. For a single meridian, four mirrors 1 and 2 are used which can have any angular configuration but for ease of alignment. The central mirrors 2 can be rod mirrors between 10 and 80 degrees while the outer minors 1 are the controlling mirrors to generate the angle 7 of the probing beam necessary. These minors may have the exact and opposite angle to each other with respect to the optical axis 4.

The separation between the two inner mirrors 5 must be sufficiently large enough to allow an axialized beam to enter and return, this is of course dependent on the arrangement of the optical system 3 being measured. The separation between the two outer minors 6 is dependent on the distance to the optical system and the angles to which they probe the surfaces. However, the converse is also true and the separation distance can be left at a set distance and the optical system must then lie within the probing range. It must be noted that the separation is suited to a large value as this will reduce the risk of any interference with mechanical or optical parts. The diameters of the mirrors can be designed to whatever is necessary however, the diameter of the inner mirrors determines the diameter of the probing beams. At all times the position and angles of the mirrors must be rotational symmetric about the optical axis for the conditions of the three types of reflections to hold true.

Figure 4:
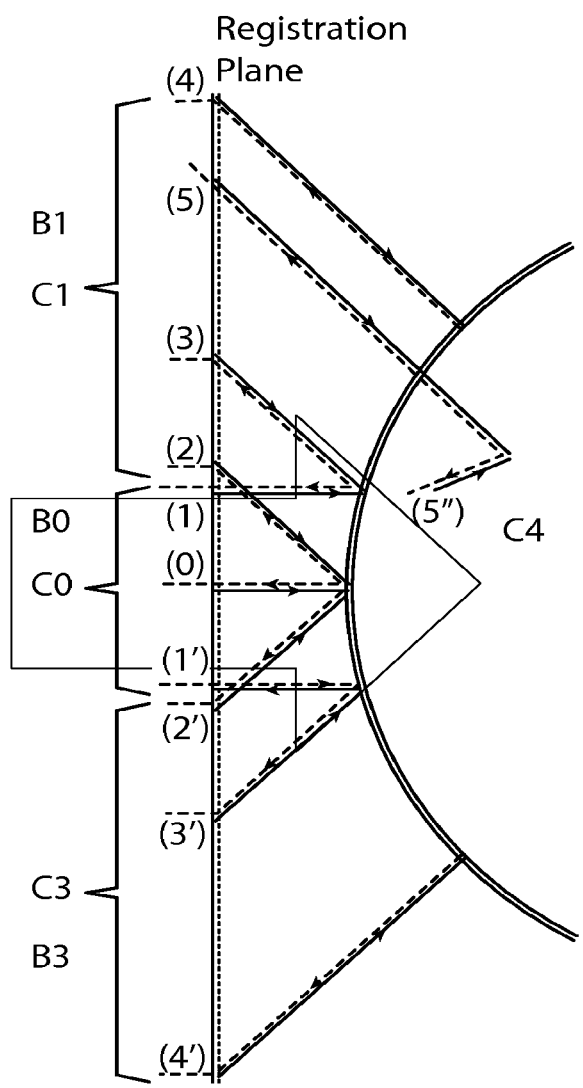
FIG. 4 is a detailed view of the collimated beams in accordance with the present invention used to illuminate the surface of the eye.

In a preferred embodiment, as shown in FIG. 4, five broad collimated beams are used to illuminate the eye, namely, Bl and B3 in the vertical meridian (VM), and B2 and B4 in the horizontal meridian (HM) and BO in the central. The use of these five beams allows the required parameters to be determined simultaneously. The back reflected light is imaged through the same five channels: CI and C2 in the VM; and C3 and C4 in the HM; the central CO. From a single surface there are a plurality of reflections, at least four of which are described below. These four reflections are the main types of back reflections, namely:

1) Retro-reflection RET (light goes back through the same channel);
2) Cat-eye reflection CAT (light goes back through the opposing channel);
3) a Inner-axialised reflection AX (light goes into the central channel and returns through the outer channels);
3) b Outer-axialised reflection AX (light goes into the outer channels and returns through the central channel);
4) Oblique reflection OB (light reflects from an oblique meridian passing from a vertical channel into one of the horizontal channels and vice versa).

It will be appreciated that it is not possible to show the horizontal meridian in the two dimensional drawing of FIG. 4, however this figure depicts the vertical meridian with three illuminating beams BO, Bl, and B2 and corresponding three imaging channels CO, CI, and C3. There are five back reflections (all being AX) registered in the central channel CO, however only three are shown as 0, 1 from Bl and from B3 Channel CI has also five reflections however for the purpose of illustration, only four are shown: CAT from B3, 2, AX from BO, 3, RET from Bl, 4, and OB from B4, 5, where the beam B4 is passing along the channel C4, both in the HM. Similarly, channel C3 has five reflections, only three along the vertical direction are shown: CAT from Bl, 2', AX from BO, 3', and RET from B3, 4', the remaining two reflections will be of OB type coming from B2 and B4 Channel C4 has 5 reflections however only one is shown namely OB from Bl, 5". As all five channels have five reflections each, twenty-five reflections in total are available for measurements. Reflections 1 and 3 can be distinguished as inner AX reflection and outer AX reflection, respectively. It will be appreciated that a combination of these reflections may be used in determining and measuring optical surface properties. The combination of the structures described above provide the ability to measure different types of reflections and to reconstruct surfaces in a single pass without the need to obtain multiple measurements individually.

Figure 9:
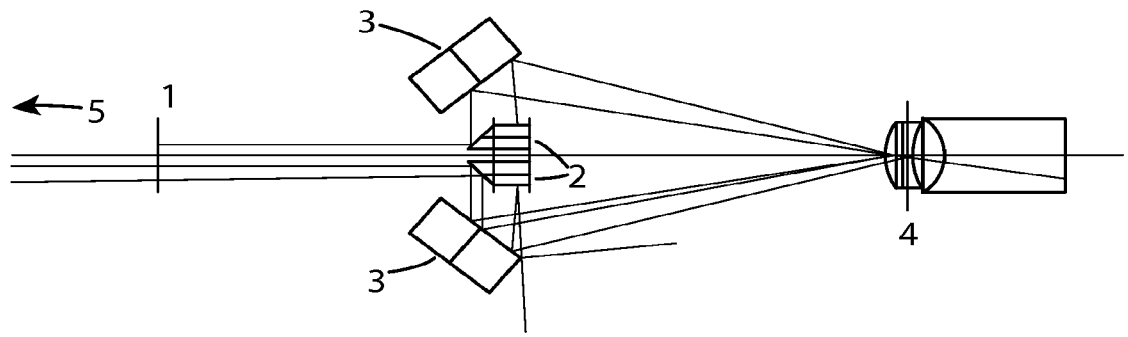
FIG. 9 shows Cat-eye reflection within a Purkinje system in accordance with one embodiment of the present invention.
Figure 10:
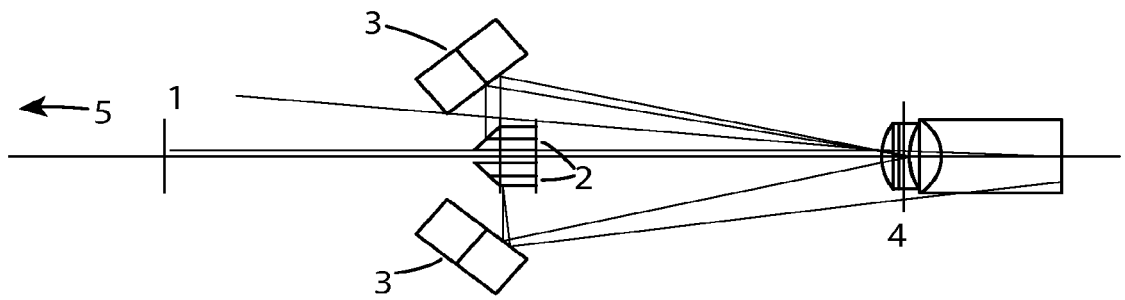
FIG. 10 shows Axialised reflection within a Purkinje system in accordance with one embodiment of the present invention.
Figure 11:
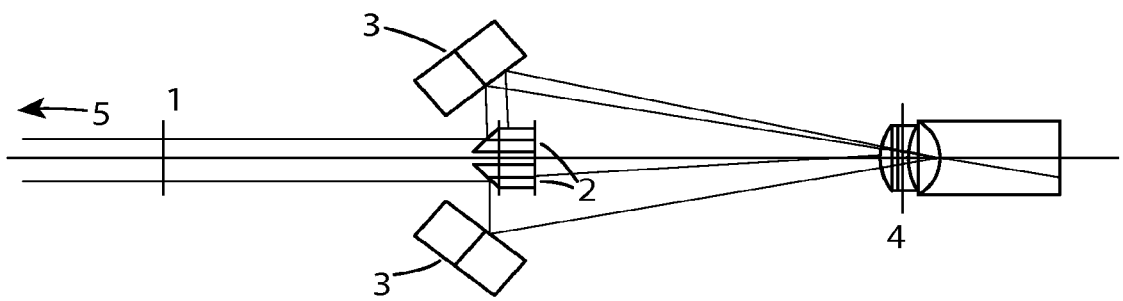
FIG. 11 shows Retro reflection within a Purkinje system in accordance with one embodiment of the present invention.

FIGS. 9-11 show three different types of back reflections within a Purkinje System, wherein a collimated (possibly infrared) source from 1 illuminates the rod mirrors 2. Rays are then reflected by the rod mirrors going to the Mirricon mirrors 3 and reflected again towards the eye 4 at a specific angle. FIG. 9 shows Cat-eye reflection, FIG. 10 shows Axialised reflection, and FIG. 11 shows Retro reflection.

A Cat-eye reflection is from the apex of a surface and returns via the mirrors of the opposite side to that which was originally illuminated. The cat-eye reflection serves the main purpose to anchor the position of the apex of the surface to be characterized with respect to the Mirricon along its optical axis. For the anterior corneal surface, the cat-reflection gives the position of the eye with respect to the Mirricon, while the cat-eye reflections for the following surfaces gives the information about the central (axial) thickness value entangled with the refractive index of the corresponding medium.

A Retro reflection occurs when a particular zone of the surface appears normal to the beam and reflects back onto itself by the same path it was illuminated. An Axialised reflection is incident at a zone where the angle of reflection is such that it returns to the mirrors parallel to the optical axis of the instrument, and passes through the gap between the rod mirrors. It will be appreciated that axialised reflection also works in the reverse direction, i.e. the surface in question is illuminated via the gap between the rod mirrors and returns via the mirrors at the same angle and positions as when they were illuminated from the mirrors. The Retro and Axialised reflections relate information on the curvatures, refractive indices and separations of the surfaces in the eye.

The main principle of these reflections is that when rays strike a surface of the eye, to be modelled either via the mirrors or directly, they will return either via the mirrors or directly and pass on to the telecentric arm 200 in FIG. 2.

Figure 5:
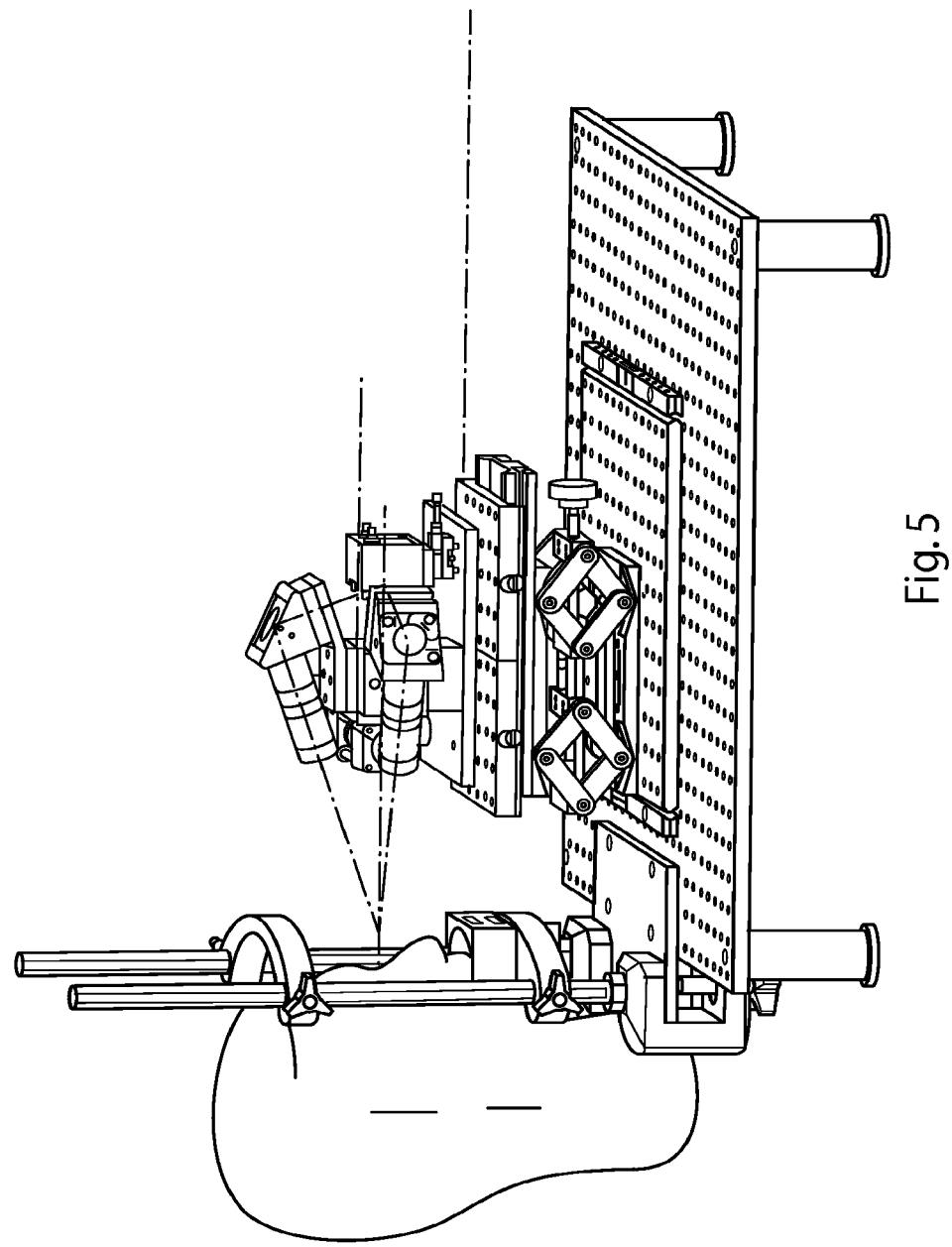
FIG. 5 is a representation of a system in accordance with one embodiment of the present invention.
Figure 12:
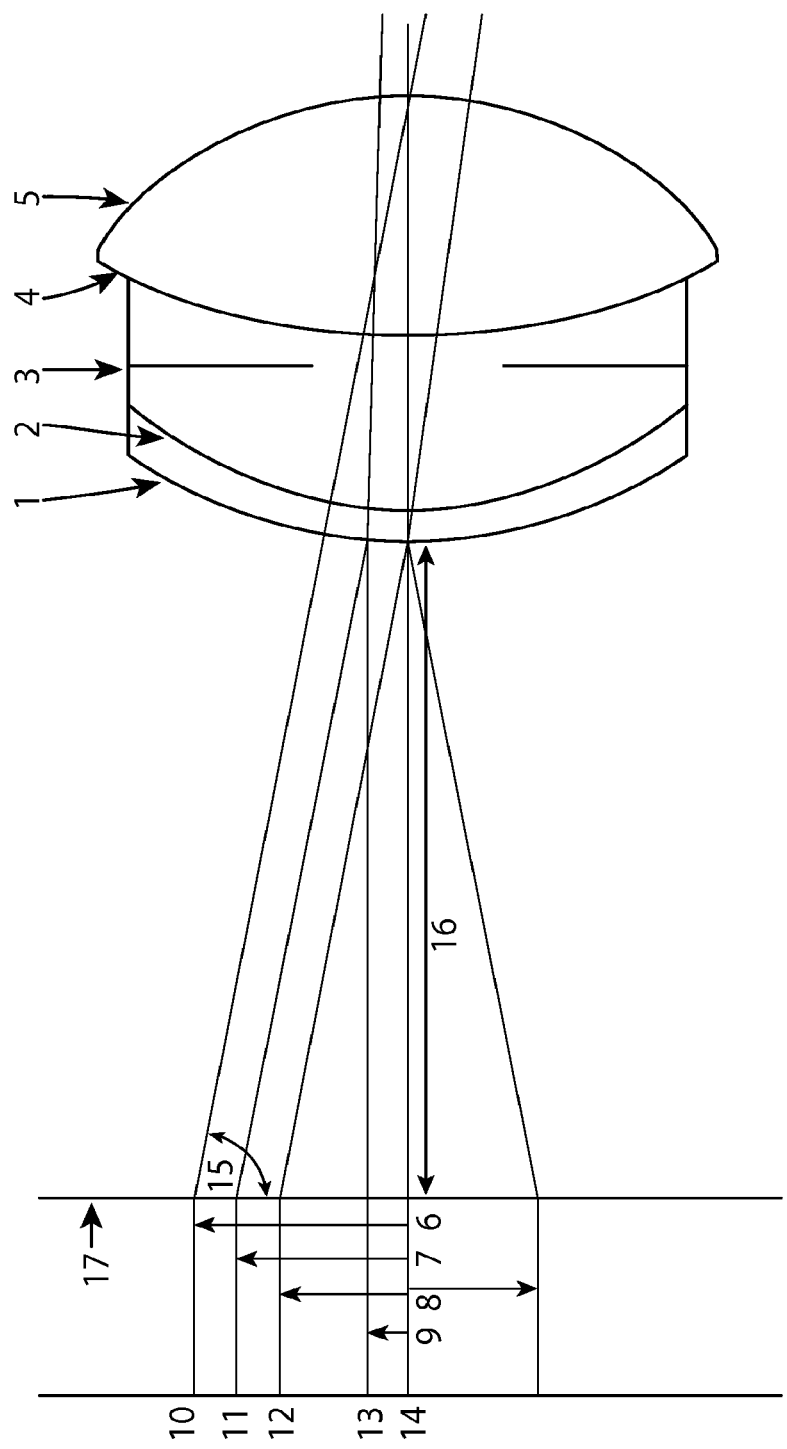
FIG. 12 is a generalised structure of the eye showing the details of Ray heights with reference to an eye structure.

In FIG. 12, a generalised structure of the eye and the relevant measurements used in determining this structure their optical parameters are outlined. These are the anterior cornea, 1, the posterior cornea, 2, the iris, 3, the anterior lens, 4 and the posterior lens, 5. are depicted in FIG. 5. To effectively determine the optical surface parameters, heights of aforementioned rays are required. These include as seen in FIG. 12, $H_{ret}$ height of retro reflection, 6,
$H_{axi\ out}$ height of outer axialised reflection, 7,
$H_{cat}$ height of Cat-eye reflection, 8
$H_{axi\ in}$ height of inner axialised reflection, 9
retro reflection beam, 10
axialised reflection beam, 11
cat-eye reflection beam, 12,
axialised reflection beam, 13
instrument optical axis, 14
$\Theta_{beam}$ input beam angle, 15.

Figure 13:
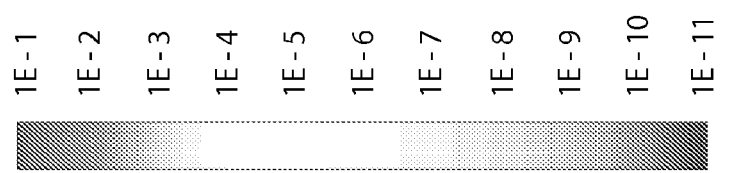
FIG. 13 shows Purkinje reflections for a single surface as seen on the detector.
Figure 13:
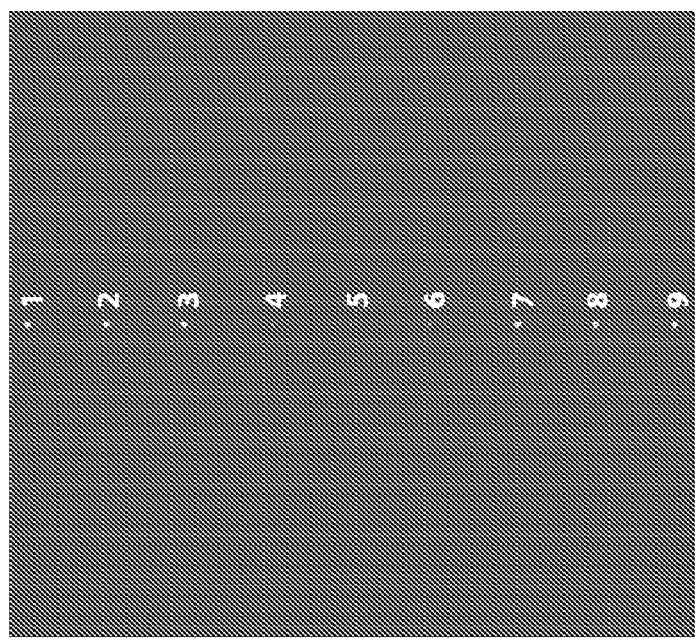
Figure 14:
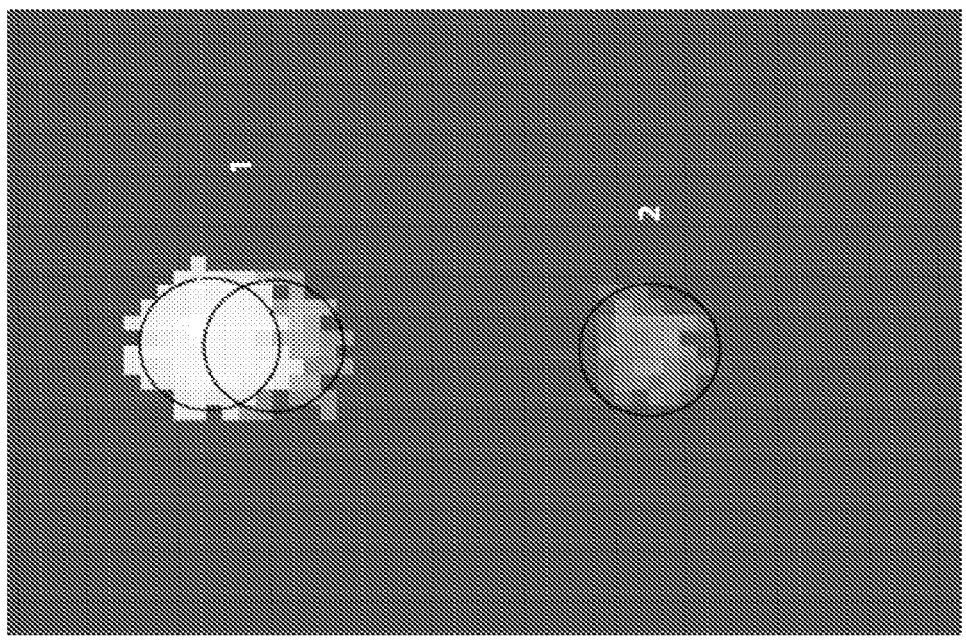
FIG. 14 demonstrates centroiding of spots by which the ray heights are measured.

Using the system and methods above these measurements can be obtained and used to determine the parameters of various structures of interest. In Key to determining the properties of any ocular surface, it is necessary to measure where each type of reflection strikes the beam plane, e.g. 17 in FIG. 12. This is then conjugated with a telecentric system and the necessary magnification is appropriated for the functional use of the instrument and the size of the detector to hand. A sample image for a single surface is shown in FIG. 13 and points out the locations of each type of Purkinje reflection from which the relevant heights of the reflections can then be measured on the detector. FIG. 14 shows a magnified view of these Purkinje reflections and the centre of which needs to be found for accurate determination of the height. Determination of these centroids is worked either on a curve fit of the spot at a threshold or a weighted mean. The threshold for the curve fit is set to a brightness level where an interfering second surface reflection can be eliminated or minimized. The centroid is then the centre of the circumference of that spot. A weighted mean will not work in this scenario as the second overlapping spot will shift the centroid to the centre of gravity of the combined spots. Overlapping spots occur when thicknesses between surfaces are small.

In an exemplary method of determining the radius of the anterior cornea, re the following equations may be implemented based on the measurements 6 to 15 of FIG. 12 determined using for example the ray reflection techniques in FIGS. 2 to 4. It will be appreciated that alternatively an optimisation algorithm could also be used to take into account an additional meridian.

As a first step, the radius of the anterior cornea is calculated. The beam heights are recovered from the distance of separation between the centroids of the reflections from the respective reflections as viewed on the detector 201, example centroid seen in FIG. 14. The anterior cornea curvature can be calculated in a number of ways.

$$r_c = \tan(\theta_{beam})H_{ret} - Z \quad \text{EQ (1)}$$

$$Z = \tan(\theta_{beam})H_{cat} \quad \text{EQ (2)}$$

$$r_c = \tan(\theta_{beam})(H_{ret} - H_{cat}) \quad \text{EQ (3)}$$

$$r_c = H_{axi\,in}/\sin((90 - \theta_{beam})/2) \quad \text{EQ (4)}$$

$$r_c = \frac{Q_{axi\,out}}{\sin((\theta_{beam} - 90)/2) + \sin(\theta_{beam} - 90)} \quad \text{EQ (5)}$$

Using these calculations of the cornea and the above listed details, rays tracing equations can then be used to determine the central corneal thickness, CCT, $$CCT = (1 - \cos(\theta_i - U))r_c + \frac{\sin(\eta_{beam})\sin(\theta_i - U)r_c}{\sin(90 - \eta_{beam})} \quad \text{EQ (6)}$$

where $$\eta_{beam} = \theta_{beam} - \theta_i + \theta_r \quad \text{EQ (7)}$$

$$U = \theta_{beam} - 90 \quad \text{EQ (8)}$$

$$\theta_i = \arcsin\left(\frac{Q_{cat\,post\,corn}}{r_c} + \sin(U)\right) \quad \text{EQ (9)}$$

$$\theta_r = \arcsin\left(\frac{n_{air}\sin\theta_i}{n_{corn}}\right) \quad \text{EQ (10)}$$

$$Q_{(surface)} = H_{(surface)}\cos(U) - z\sin(U) \quad \text{EQ (11)}$$

As the term ncorn is an unknown it is necessary to determine an iterative solution in order to find it and the CCT.

A time of flight measurement (τ) of the CCT obtained from OCT and a solution of the equation below will yield the CCT and ncorn is determined from using the equation below.

$$\tau - n\text{corn}CCT = 0 \quad \text{EQ(12)}$$

The equations above are solved for the convention of Figure FIG. 512. It will be appreciated that with rays entering from the underside, the equations will require slight modification to hold the sign convention.

In determining the characteristics of any surface there after, it is necessary that each successive surface has the preceding surface characterized for its respective index, curvature and distance to the next surface. Distances may be determined from the relationship between the beam angle, the anterior corneal curvature calculated, the height of the reflections of the internal structures and refractive indices of the media through which the beams traverse. Refractive indices can be recovered from the time of flight measurements. Alternatively, the differential brightness of the reflections, given that the mediums before and after the lens (air and aqueous) has a fixed refractive index and the refractive index between the cornea and the lens (aqueous) is also fixed, will allow derivation of refractive index by means of Fresnel equations which are a function of refractive indices, angle of incidence of beams as calculated by the angle of the beams, beam heights and radius of curvature of the two different surfaces. As refractive indices are functions of wavelengths, a dispersion curve is used to calculate the change in refractive index given a specific wavelength of source light rays used. Another alternative in determining the refractive index could be based on using axialized and oblique reflections along with the cat-eye and retro reflections and then solving for the radius of curvature, thickness and refractive index simultaneously.

In determining the curvature of the next surface, the following steps may be implemented. It will be appreciated that these equations are typical of ray tracing in a given meridian through the reconstructed part of the optical system of the eye.

1. Identify the Purkinje reflection of the next surface
2. Measure the height of the retro reflection
3, Find y, z, $\theta_r$, $\eta_{beam}$ knowing $r_c$ and n
4. Apply EQ (1) above where. $\theta_{beam}$ is new $\eta_{beam}$, is now y and z is CCT-x $$y = \sin(\theta_i - U)r_c \quad \text{EQ (13)}$$

$$x = (1 - \cos(\theta_i - U))r_c \quad \text{EQ (14)}$$

$$R_c = \frac{Q'_{axi\,in} + Q'_{axi\,out}}{(\sin(U'_{axi\,in}) + \sin(U'_{axi\,out}))} \quad \text{EQ (15)}$$

This approach may then be used to determine the radius, thickness and refractive index of each successive surface in the optical system. It will be appreciated that these equations are depictive of meridional ray tracing which provides a solution for the unknown shape parameters (including ray and possibly asphericity) of the selected surface in the eye. Alternatively, ray-tracing can be used to reconstruct the measured eye parameters.

To determine the properties for other meridians of the optical system in question all one can do is rotate the probing beams about an axis that is most likely to be the optical axis of the instrument. Alternately, the minimum number of meridians to determine the biconic values of the surface (cylinder) is three, vertical, horizontal and ±45°. These can also in themselves be rotated, hence the detector will see three rotating lines of spots. The number of simultaneous probing meridians is limited only by the mechanics of the system where the mirricon is concerned. The Axicon will yield a set of rings instead of spots and the number of meridians is limited then by the resolution of the detector, if not unlimited.

To determine the asphericity of the surface in question, differing angle of a probing beam for the same meridian should be used. This will then give a local radius for more points along the curve and then give a higher precession q value. This is not to say that a single angle probing beam cannot complete the same task however it will not be as reliable as multiple angle probing beams will yield a result with higher accuracy. Along this line of thought, the combination of the differing angles for the mirricons in tandem with the rotating mirricon can determine the asphericity and cylinder of the surface.

A Scheimpflug system can also be used for the determination of ocular parameters. Typically, in a standard configuration Scheimpflug systems allow for the possibility of diagnosis of the front chamber of the eye and in particular the front surface of the cornea using a large incident beam angle to provide a large field of view and larger curvatures. Scheimpflug optical systems adhere to the Scheimpflug principle wherein the plane of the object, the main plane of the camera lens system and the image plane intersect in a common axis. To obtain more than one meridian, traditional instruments are rotated thereby requiring moving parts. The large incident beam angle and large curvatures facilitate this movement without losing accuracy.

Figure 6:
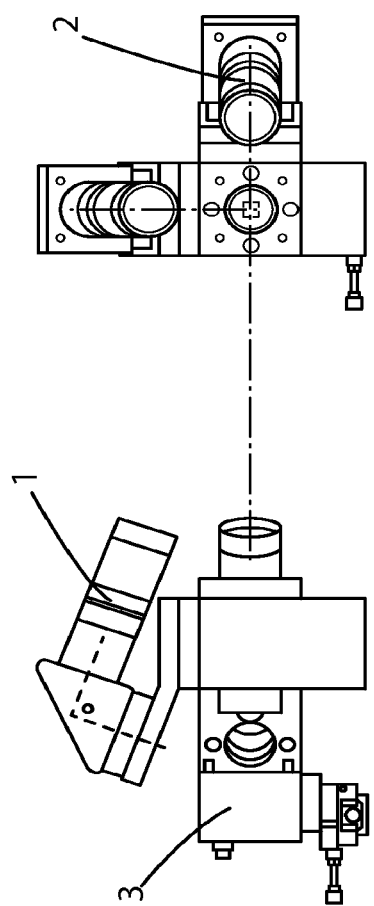
FIG. 6 is a model of a Scheimpflug system in accordance with the present invention.
Figure 7:
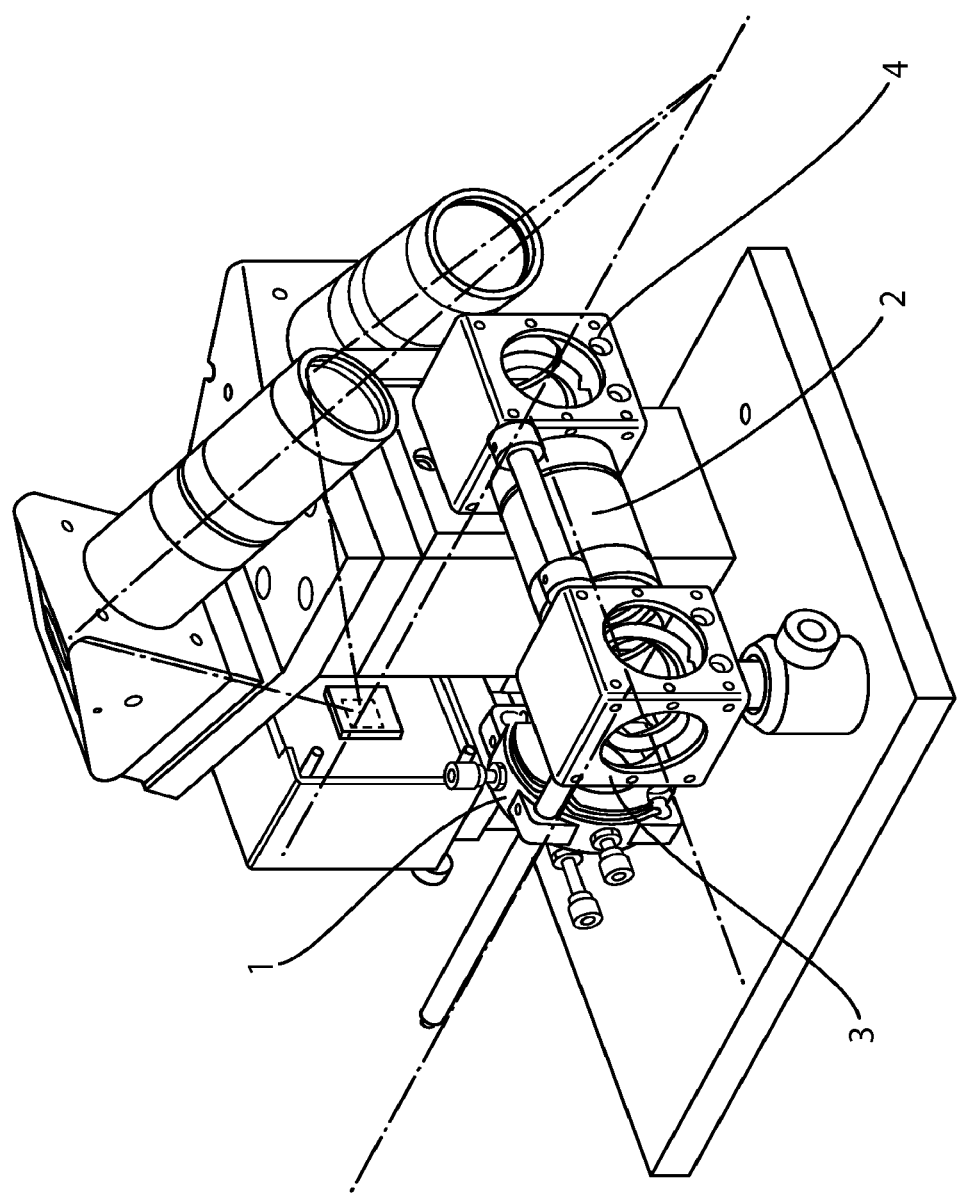
FIG. 7 is an alternative view of a Scheimpflug system in accordance with the present invention.
Figure 8:
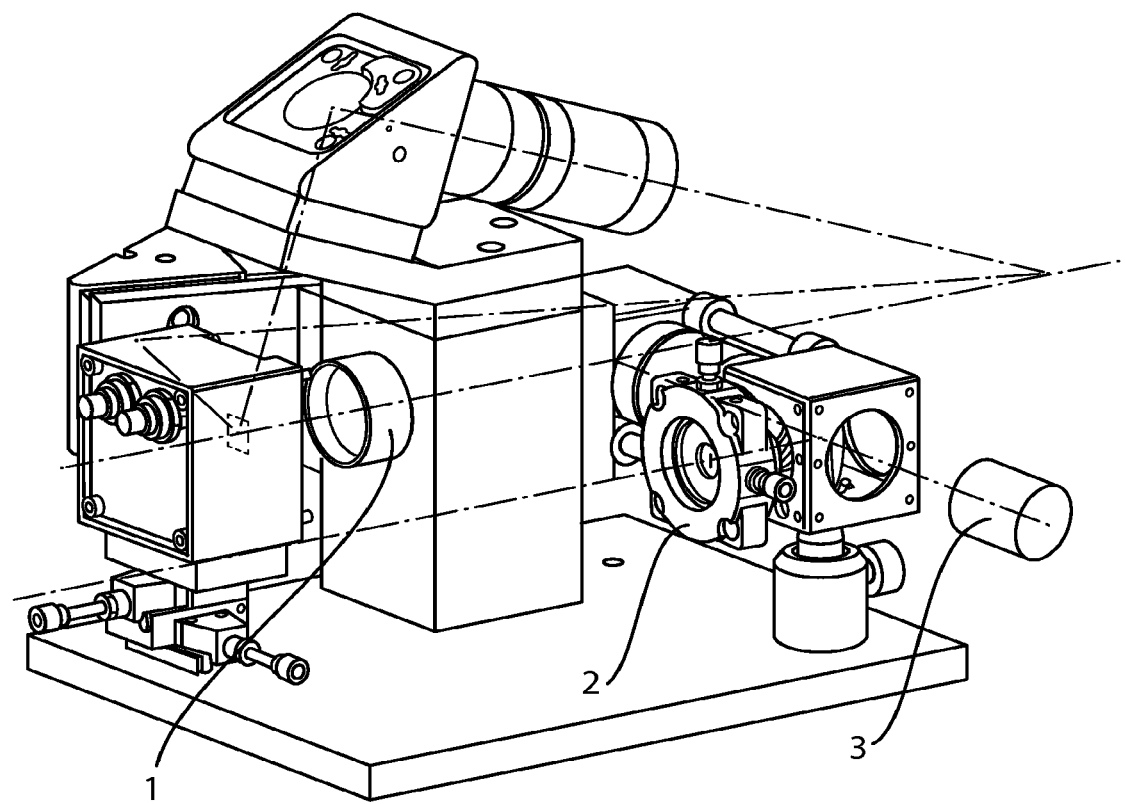
FIG. 8 is a third view of a Scheimpflug system in accordance with the present invention.

As shown in FIGS. 6, 7 and 8, a Scheimpflug system in accordance with the present invention provides for a smaller incident beam angle to facilitate greater depth penetration into the eye. FIG. 6 shows the bottom view (on the left-hand side) and the top view (right-hand side) of a dual-arm Scheimpflug system in accordance with the present invention. The first arm, 1 images the vertical meridian of the eye, while the second arm, 2 provides imaging for the horizontal meridian of the eye. Both arms deliver the images of the vertical and horizontal meridians on the same detector, 3. FIG. 7 shows a detailed view of an opto-mechanical system, in particular the illumination unit, which contains a light source unit, 1 that generates two narrow beams. A relay lens unit, 2 in conjunction with beam splitters, 3, 4 delivers the illumination into the eye for the vertical and horizontal meridians. A subject's eye positioned in front of the beam splitter, 4 is illuminated by the two narrow beams.

In contrast to traditional Scheimpflug systems using a single narrow beam, a cross hair light source (forming the two beams) is implemented in the unit, 1 shown in FIG. 7. Rays are converged from more than one meridian to the same detector using the two Scheimpflug arms. By converging the rays from more than one meridian to the same detector the need to rotate the instrument is eliminated. In addition the integration of an eye tracker on the detector axis (shown schematically as pupil camera unit 1 in FIG. 8), also eliminates the need for more than one camera or detector as the use of the eye tracker assists in centration of the eye with respect to the instrument. The images obtained with the eye tracker provide information about relative position of the two narrow beams (in the vertical and horizontal meridians) relative to the center of the pupil of the eye.

As shown in FIG. 8, a cross hair light source can be made by combining two channels, 2 and 3 that contain a vertical slit and a horizontal slit, respectively. These slits help to form very narrow beams projected by the opto mechanical unit (in FIG. 7) on the cornea. Beam splitters, 3 which may be pellicle beam splitters or parallel plate beam splitters, 4, are configured to split pupil camera (eye tracker) and illumination (splitter 3) beams and for bundling of vertical and horizontal slit illumination beams (beam splitter 4). Use of the slit illumination beams, enables a thin line in two perpendicular directions to be projected within a short period of time (or simultaneously) by synchronizing the light sources in channels (2) and (3) in FIG. 8. The light source can be pulsed so that images of the two meridians in the eye can be obtained simultaneously or one after the other if needed.

In the system in accordance with the present invention,
a) An incident beam angle of less than 40 degrees is used. This incident beam angle is the angle between Scheimpflug optics axis and the axis of the eye. This narrow angle results in the front and back surface of crystalline lens becoming visible and measurable even for non-dilated eyes. It will be appreciated that this angle of incident beam allows the posterior lens curvature to be used and that this data is then used in a reiterative manner using the equations outlined above to obtain true posterior lens curvature by considering optical characteristics of tissues in front of it.
b) The resulting truncated beam height guarantees that the edges of the beam is visible and traceable in order that the path of light through ocular tissues can be studied and used as a basis for raytracing of the marginal or zonal ray of the illumination beam in the effort to reconstruct the optical structure of the human eye.
c) For the purpose of b) a slit beam comprising of multiplicity of slits in broken lines (e.g. slits with adjustable length or segmented structure like a dashed line) configuration may also be used. The use of a visible or invisible fixation target, which may include a blinking light on which the eye can focus, allows accurate determination of visual axis, as images are taken through the centre of the eye. This fixation target may be incorporated in to the actual design of the source slit whereby the centre of the beam consists of a dot in the middle of the line (or broken, dashed lines) or spliced in using a beam-splitter.
d) The combination of a patterned source and a single detector (single CCD) which captures from multiple arms results in no overlay error.

The configuration of the present invention described uses a multiple or dual-arm Scheimpflug system which allows an image of multiple e.g. two and perpendicular) meridians of the eye within a short period of time (or simultaneously) on the same sensor chip or multiple sensor chips to be obtained.

Further features of this system include:
Multiple or dual Scheimpflug system allow to get image of multiple (e.g. two perpendicular or less than 90 degrees or more than two) meridians of the eye within a short period of time (or simultaneously) on the same sensor chip or multiple sensor chips.
The shallow Scheimpflug angle (an angle between Scheimpflug optics axis and eye axis) of less than 40 degrees. As a result of this fact front and back surface of crystalline lens become visible and measurable even for non dilated eyes.
Slit illumination project allowed to project a thin line in two perpendicular or more than two directions of less than 90 degrees apart within a short period of time (or simultaneously).
On axis eye tracking camera with own illumination system.
Triggering circuit allowed to trigger all three channels (two Scheimpflug and on axis eye tracking) independently and synchronizes with slit illumination projector.

Figure 16:
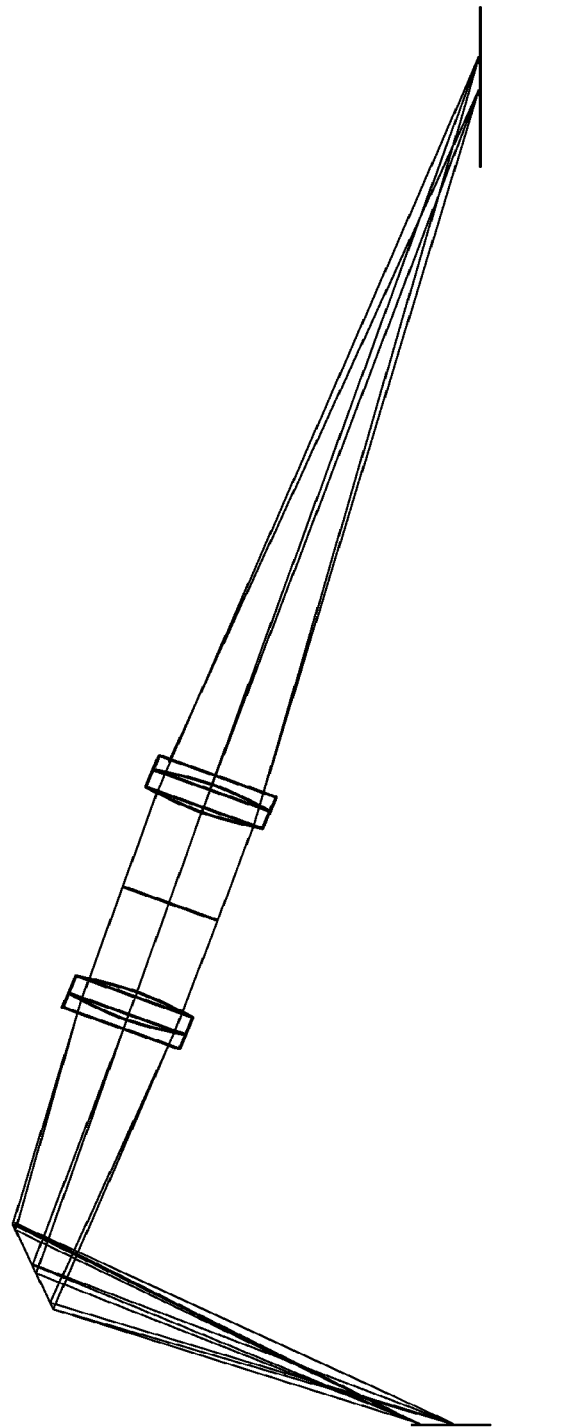
FIG. 16 is a Zemax drawing for vertical/horizontal Scheimpflug camera.
Figure 17:
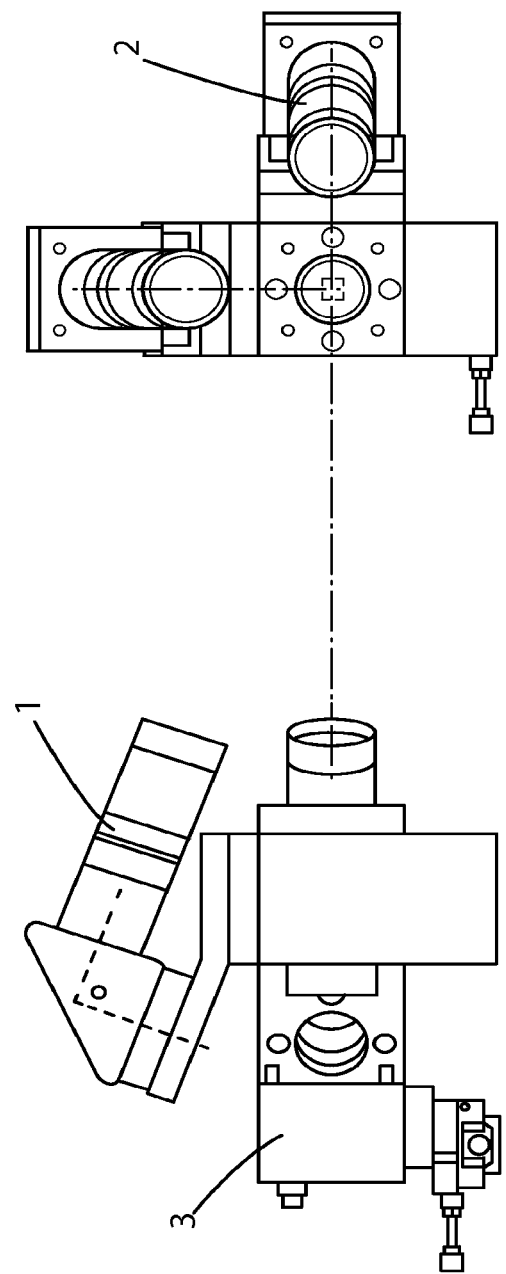
FIG. 17 shows a CAD model of a Scheimpflug camera.

FIGS. 16 and 17 show different models of a Scheimpflug camera.

Figure 18:
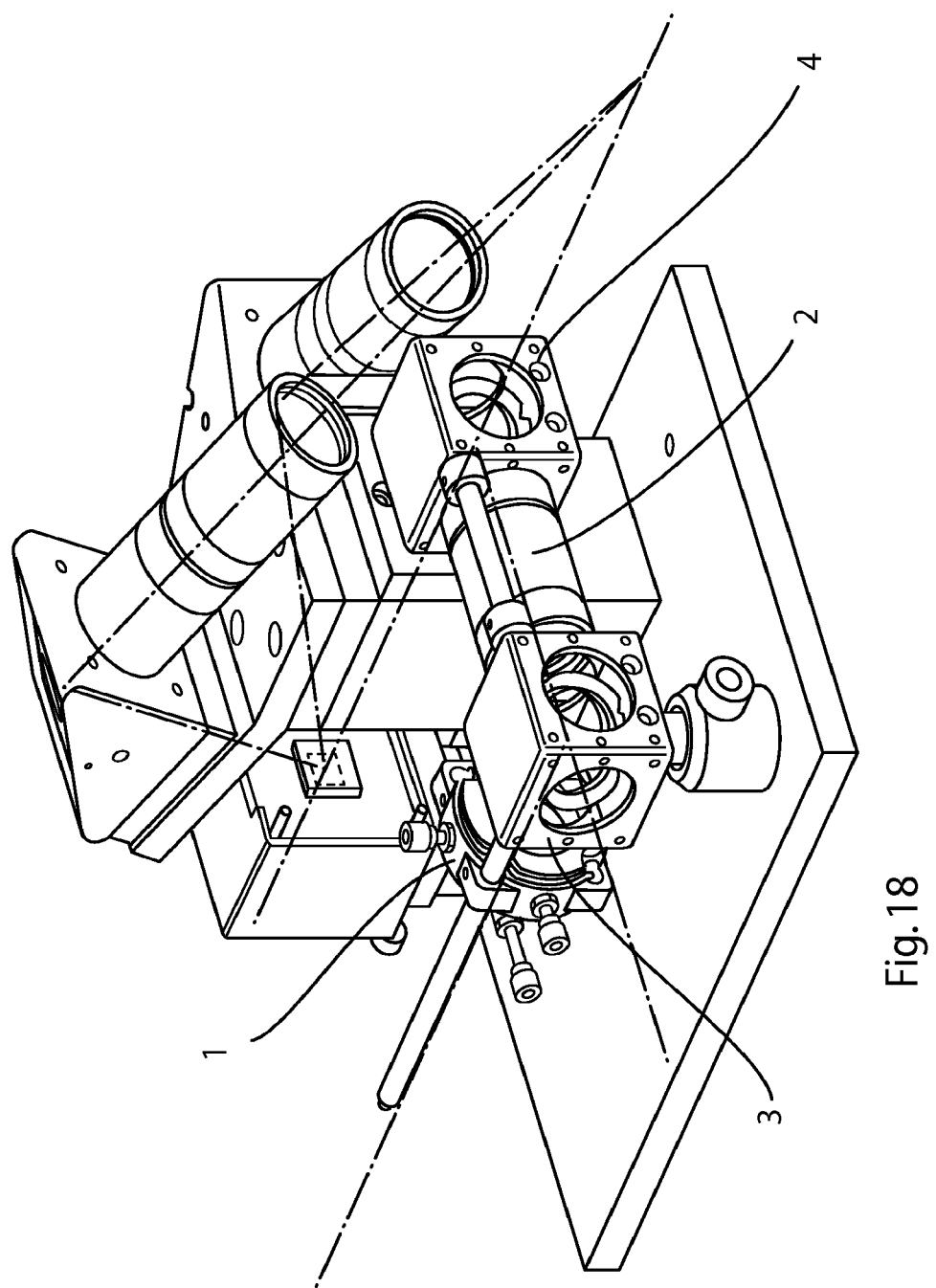
FIG. 18 shows a CAD model of a Scheimpflug system in accordance with one embodiment of the invention.
Figure 19:
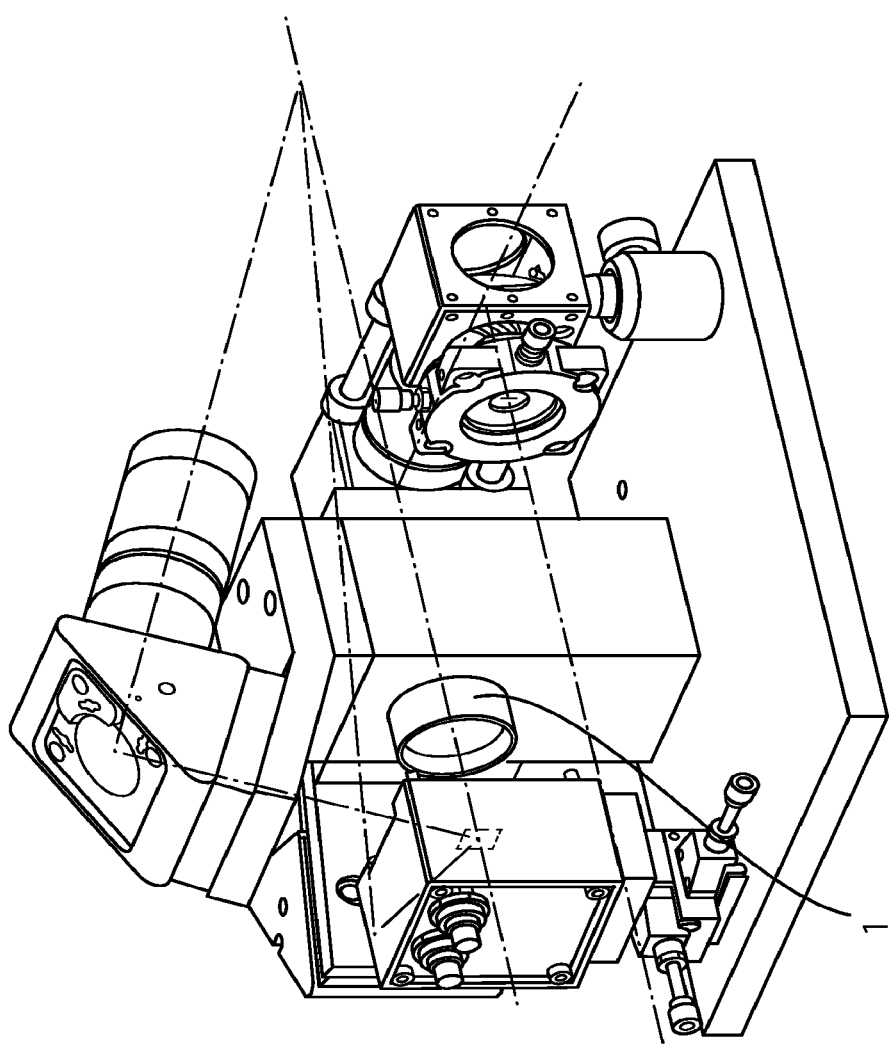
FIG. 19 shows a further CAD model of Scheimpflug system in accordance with one embodiment of the invention.
Figure 20:
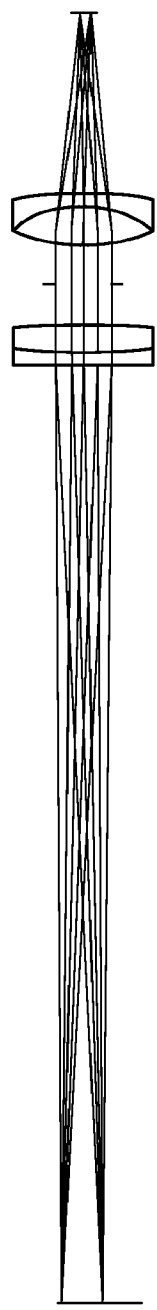
FIG. 20 is a Zemax model of a pupil camera.
Figure 21:
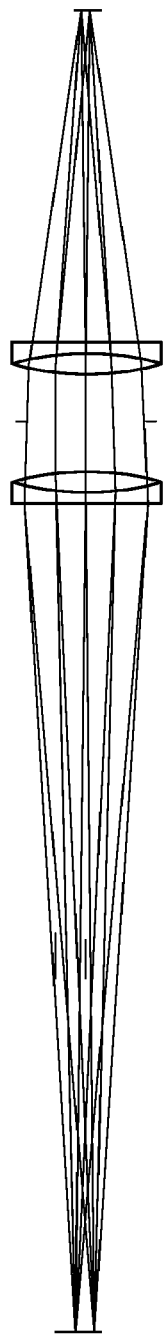
FIG. 21 is a Zemax model of a slit projector.

FIG. 18 shows one embodiment of Scheimpflug system in accordance with the present invention. The slit 1 projected by optics 2 on to the cornea. Beam splitter 3 using for splitting pupil camera and illumination optics beams, Beam splitter 4 using for bundling of vertical and horizontal slits illumination beams.

The present application discloses a real dual (90 degrees angle or less between two meridians) Scheimpflug system with single CCD chip allowing recovery of two cross sections of the cornea and crystalline lens simultaneously.

In a further refinement of the systems described above, an A-phase OCT can be combined into a single solution to improve the accuracy of the measurements recorded. It will be appreciated that an A-phase OCT can be used separately to the Scheimpflug or Purkinje systems described above to obtain the axial lengths used in the calculations above.

As an alternative to the Scheimpflug and Purkinje systems outlined above, a B-Phase OCT may be used to make the relevant measurements necessary for an accurate 3 dimensional model of the eye.

The present document describes software and hardware methods to achieve the aims as set out in the background to the invention. Several alternative optical techniques may also be employed to similar results such as optical coherence tomography, specular interferometry and second harmonics imaging. Data proxy to refractive index can also be obtained using non-optical methods such as high-frequency ultrasound and various radiological methods (computed tomography and magnetic resonance imaging).

A universal software allowing capture and analysis of above device is disclosed. Pre-requisites of such a software includes a) Correction of optical distortions from preceding surfaces b) recovery of refractive index from dispersion curve of ocular tissue using another optical measurement of another wavelength or by resolving the discrepancy in curvature or distance when compared to another optical measurement of similar wavelength c) Averaging capability of curvatures d) calculating internal ocular parameters such as effective lens position using above output parameters.

It should be appreciated that various techniques described herein may therefore be used to design lenses, for example including lens implants. The techniques may apply to designing various types of lenses, including, but not limited to, plano, convex, concave, multifocal (refractive, diffractive, etc.), toric, accommodative, prismatic, multiple lens configurations, variable curvature (e.g., aspherical), phakic intraocular lenses, light adjustable lenses, or any combination of those listed.

Additionally, one or more of the techniques described herein may be used in the context of planning or performing various types of surgeries. Such surgeries may include, but are not limited to, cornea/refractive surgery, lens surgery and retinal surgery. Various types of refractive surgery may include, but are not limited to, myopic, hyperopic and presbyopic LASIK, LASEK, or PRK, conductive keratoplasty, radial keratotomy or a combination of the above.

It should be appreciated that the various aspects described above are not limited to human eyes, but rather may be applied to any type of eye, including human eyes or any other animals. In addition, while various aspects have been described as relating to structures of the eye and implants for the eye, it should be appreciated that the techniques may also apply to additional elements, such as glasses, contact lenses, or other elements used for ocular purposes.

As previously mentioned, it should be appreciated that the methods and apparatus described above may be used to form a model of any number of structures of interest within an eye. For example, according to some embodiments, a complete model of the eye may be formed. In other embodiments, a model of a single structure (e.g., the lens, or a surface of the lens) may be formed. In still other embodiments, the methods and/or apparatus described above may be used to determine a single parameter of interest of a structure.

Thus, individual acts of the methods described above may be used for some applications, irrespective of whether the other acts are also performed.

The above-described embodiments of the present technology can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be genetically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above. In this respect, it should be appreciated that one implementation of the embodiments of the present technology comprises at least one computer-readable storage medium (e.g., a computer memory, a floppy disk, a compact disk, a tape, a flash drive, etc.) encoded with a computer program (i.e., a plurality of instructions), which, when executed on a processor, performs the above-discussed functions of the embodiments of the present technology. The computer-readable storage medium can be transportable such that the program stored thereon can be loaded onto any computer resource to implement the aspects of the present technology discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the technology.

While various inventive embodiments have been described and illustrated herein, those of ordinary skill in the art will readily envision a variety of other means and/or structure for performing the function and/or obtaining the results and/or one or more of the advantages described herein, and each of such variations and/or modifications is deemed to be within the scope of the inventive embodiments described herein. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present technology are directed to each individual feature, system, article, material, kit, and/or method described herein. In addition, any combination of two or more such features, systems, articles, materials, kits, and/or methods, if such features, systems, articles, materials, kits, and/or methods are not mutually inconsistence, is included within the inventive scope of the present disclosure. All definitions, as defined and used herein, should be understood to control over dictionary definitions, definitions in documents incorporated by reference, and/or ordinary meanings of the defined terms. The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternative (i.e., "one or the other but not both") when preceded by terms of exclusivity, such as "either," "one of," "only one of," or "exactly one of." "Consisting essentially of," when used in the claims, shall have its ordinary meaning as used in the field of patent law. As used herein the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than, B (and optionally including other elements); etc. It should also be understood that, unless clearly indicated to the contrary, in any methods claimed herein that include more than one step or act, the order of the steps or acts of the method is not necessarily limited to the order in which the steps or acts of the method are recited. In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of and "consisting essentially of shall be closed or semi-closed transitional phrases, respectively, as set forth in the United States Patent Office Manual of Patent Examining Procedures, Section 2111.03.

The words "comprises/comprising" and the words "having/including" when used herein with reference to the present invention are used to specify the presence of stated features, integers, steps or components but does not preclude the presence or addition of one or more other features, integers, steps, components or groups thereof. It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

What is claimed is:

1. A method of imaging an optical element with an optical axis, the method comprising: illuminating a targeted optical element with at least one collimated incident light beam; altering the direction of incidence of at least one incident light beam on the targeted optical element; directing, with at least one telecentric optical system and a plurality of mirrors angularly oriented with respect to the targeted optical element on opposing sides of an optical axis of the telecentric optical system, plurality of returning light beams returning at predetermined angles from at least one surface of the illuminated optical element onto at least one detector, wherein the plurality of mirrors are oriented such that the plurality of returning light beams are directionally reflected from the mirrors towards the targeted optical element at a specific angle of reflection selected such that a Purkinje reflection is present in the image and the plurality of returning light beams are separated from each other by sufficient magnitude such that the reflections are resolvable in a crowded group; measuring relative light characteristics of the plurality of returning light beams; and calculating at least one parameter of the optical element using the measured characteristics of the plurality of returning light beams.

2. The method of claim 1, further comprising:
    splitting at least one beam of light emitted from an illumination source, wherein at least two of the resultant split beams have a different angle of incidence relative to the optical axis of the targeted optical element.

3. The method of claim 1, wherein altering the direction of at least one incident light beam further comprises directing the at least one incident light beam toward at least one of a beam shaping lens, mirror with optical power, fold mirror, beam splitter or prism.

4. The method of claim 1, further comprising:
    altering the direction of the returning beams with at least one of a beam shaping lens, mirror with optical power, fold mirror, beam splitter or prism.

5. The method of claim 1, further comprising:
    changing at least one characteristic of at least one incident light beam on the targeted optical element between consecutive measurements of the detector.

6. The method of claim 4, wherein altering the direction of the plurality of returning beams further comprises controlling the direction of at least one incident light beam.

7. The method of claim 1, further comprising:
    changing the position of the at least one detector to focus any or all of the returning light.

8. The method of claim 1, wherein measuring relative light characteristics of the at least two returning light beams further comprises:
    measuring at least one of spatial and temporal intensity distribution, position, spatial and temporal linear and circular polarization, degree of polarization, phase, wavelength, temporal and spatial coherence, speckles structure, scattering coefficient and g-anisotropy factors.

9. The method of claim 1, further comprising:
directing plurality of light beams returning at predetermined angles from at least one surface of the illuminated optical element onto a second detector wherein the first detector and the second detector lie on different planes with respect to the optical axis of the targeted optical element; or wherein the first detector and the second detector lie on the plane of the optical axis of the targeted optical element.

10. The method of claim 1, wherein illuminating the targeted optical element further comprises:
illuminating the targeted optical element with a cross hair light source adapted to generate two beams for projection on the optical element.

11. A method of imaging an optical element, the method comprising:
illuminating a targeted optical element with at least one collimated incident light beam wherein illuminating comprises altering the direction of incidence of at least one incident light beam on the targeted optical element; and
directing a plurality of returning light beams returning at predetermined angles from at least one surface of the illuminated optical element onto at least one detector using at least one telecentric optical system and further using a plurality of mirrors angularly oriented with respect to the targeted optical element on opposing sides of the optical axis, wherein the plurality of mirrors are oriented such that the plurality of returning light beams are directionally reflected from the mirrors towards the targeted optical element at a specific angle of reflection selected such that a Purkinje reflection is present in the image and the plurality of returning light beams are separated from each other by sufficient magnitude such that the reflections are resolvable in a crowded group;
measuring the relative light characteristics of the plurality of returning light beams and
calculating at least one parameter of the optical element using the measured characteristics of the plurality of returning light beams.

12. The method of claim 11, further comprising changing at least one characteristic of at least one incident light beam on the targeted optical element between consecutive measurements.

* * * * *